US011913956B2

(12) United States Patent
Wang (10) Patent No.: US 11,913,956 B2
(45) Date of Patent: Feb. 27, 2024

(54) TUMOR BLOOD MARKER, USE THEREOF, AND KIT COMPRISING THE SAME (71) Applicant: SHANDONG ZEJI BIOTECHNOLOGY CO., LTD., Shandong (CN)

(72) Inventor: Zesong Wang, Shandong (CN)

(73) Assignee: SHANDONG ZEJI BIOTECHNOLOGY CO., LTD., Shandong (CN)

(*) Notice: Subject to any disclaimer, the term of this patent is extended or adjusted under 35 U.S.C. 154(b) by 331 days.

(21) Appl. No.: 16/639,125

(22) PCT Filed: Jul. 4, 2018

(86) PCT No.: PCT/CN2018/094401
§ 371 (c)(1),
(2) Date: Feb. 14, 2020

(87) PCT Pub. No.: WO2019/033866
PCT Pub. Date: Feb. 21, 2019

(65) Prior Publication Data
US 2020/0209244 A1 Jul. 2, 2020

(30) Foreign Application Priority Data
Aug. 18, 2017 (CN) .......................... 201710712539.3

(51) Int. Cl.
G01N 33/574 (2006.01)
G01N 33/68 (2006.01)

(52) U.S. Cl.
CPC ... *G01N 33/57407* (2013.01); *G01N 33/6803* (2013.01); *C12Y 102/01012* (2013.01); *G01N 33/574* (2013.01); *G01N 33/57484* (2013.01); *G01N 2333/90203* (2013.01)

(58) Field of Classification Search
CPC ......... G01N 33/57407; G01N 33/6803; G01N 2333/90203; G01N 33/57484; G01N 33/57488; G01N 2800/50; G01N 2800/52; G01N 2800/54; G01N 2800/56; G01N 33/574; G01N 33/577; C12Y 102/01012
See application file for complete search history.

(56) References Cited

FOREIGN PATENT DOCUMENTS

| CN | 1358847 | 7/2002 |
| CN | 101613760 | 12/2009 |
| CN | 104969071 | 10/2015 |
| CN | 106701801 | 5/2017 |

OTHER PUBLICATIONS

Rahman et al., Oncotarget, vol. 7, No. 34: 54852-54866, Jun. 23, 2016 (Year: 2016).*
Bedi, et al. Mol Pharmaceutics, 10:551-559, Dec. 7, 2012 (Year: 2012).*
Hao, Lihong et al., "Glyceraldehyde-3-Phosphate Dehydrogenase (GAPDH) as an Internal Reference and Its Expression in Tumors", Chinese Journal of Histochemistry and Cytochemistry, vol. 20, Issue 5, Oct. 2011, with English abstract, pp. 1-4.
Wanqing Chen et al., "Cancer Statistics in China 2015", CA Cancer J Clin , vol. 66, No. 2, Mar./Apr. 2016, pp. 115-132.
David Ramos et al., "Deregulation of Glyceraldehyde-3-Phosphate Dehydrogenase Expression During Tumor Progression of Human Cutaneous Melanoma", Anticancer Research, vol. 35, Issue 1, Jan. 2015, pp. 439-444.
Manali Phadke et al., "Accelerated cellular senescence phenotype of GAPDH-depleted human lung carcinoma cells", Biochemical and Biophysical Research Communications, vol. 411, Jul. 2011, pp. 409-415.
Craig Nicholls et al., "GAPDH: A common enzyme with uncommon functions", Clinical and Experimental Pharmacology and Physiology , vol. 39, Aug. 2012, pp. 674-679.
A Tarze et al., "GAPDH, a novel regulator of the pro-apoptotic mitochondrial membrane permeabilization", Oncogene, vol. 26, Apr. 2007, pp. 2606-2620.
Dunrui Wang et al., "The Expression of Glyceraldehyde-3-Phosphate Dehydrogenase Associated Cell Cycle (GACC) Genes Correlates with Cancer Stage and Poor Survival in Patients with Solid Tumors", Plos One, vol. 3, Issue 4, Apr. 2013, pp. 1-10.
J.X. Xue et al., "Quantitative detection of serum circulating DNA in patients with breast cancer," Monthly Convertech, Tumor, vol. 31, Issue 12, Dec. 2011, with English abstract, pp. 1-4.
"International Search Report (Form PCT/ISA/210) of PCT/CN2018/094401," dated Sep. 30, 2018, with English translation thereof, pp. 1-7.

* cited by examiner

Primary Examiner — Kimberly Ballard
Assistant Examiner — Stacey N MacFarlane
(74) Attorney, Agent, or Firm — JCIP GLOBAL INC.

(57) ABSTRACT

The present invention provides a tumor blood marker and a use thereof. Specifically, the present invention provides a use of a reagent, which is used to detect GAPDH in a blood sample, in a preparation of a detecting composition for tumor screening, risk evaluation of tumor development in subjects, distinction of tumor progression stages, identification of therapeutic efficacy of tumor and/or risk analysis of tumor progression. The present invention also provides a kit and a method for detecting GAPDH concentrations in blood samples.

11 Claims, 5 Drawing Sheets
Specification includes a Sequence Listing.

TUMOR BLOOD MARKER, USE THEREOF, AND KIT COMPRISING THE SAME

CROSS-REFERENCE TO RELATED APPLICATION

This application is a 371 application of International PCT application serial no. PCT/CN2018/094401, filed on Jul. 4, 2018, which claims the priority benefit of Chinese application no. 201710712539.3, filed on Aug. 18, 2017. The entirety of each of the above-mentioned patent applications is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Feb. 18, 2023, is named 096161-US-sequence listing_ST25 and is 5,921 bytes in size.

TECHNICAL FIELD

The present invention relates to a tumor blood marker, a use thereof, and a kit comprising the same, and specifically to a technique for diagnosis, prognosis evaluation and treating-efficacy monitoring of various tumors, such as liver cancer, lung cancer, breast cancer, gastric cancer, esophageal cancer, colorectal cancer, etc. by detecting the amount of GAPDH in human blood. The GAPDH as a marker of the present invention can be used for, but not limited to, tumor screening, risk evaluation of tumor development in subjects, distinction of tumor progression stages, identification of therapeutic efficacy of tumors and risk analysis of tumor progression.

BACKGROUND

Malignant tumors are common and frequently-occurring diseases worldwide and are one of the major diseases that endanger human health. In China, there were about 4.292 million new cases of cancer in 2015, i.e. 12,000 new cases per day on average. At the same time, about 2.814 million people died of cancer, i.e. the average number of deaths per day is 7,500. Among the cancers, lung and bronchial cancer, gastric cancer, liver cancer, esophageal cancer and colorectal cancer together account for three-quarters of all cancer deaths (CA Cancer J Clin. 2016; 66:115-132). The incidence of malignant tumors in China has been continuously increasing in recent years, and has become the leading cause of death among Chinese residents.

Glyceraldehyde 3-phosphate dehydrogenase (GAPDH) is an important enzyme in the glycolysis process, with a molecular weight of 37 kDa, catalyzing the reaction of glyceraldehyde 3-phosphate to D-glycerate 1,3-bisphosphate. In addition to its well-known metabolic regulation function, GAPDH has been shown according to recent studies that it is also involved in many non-metabolic regulatory processes, including transcriptional activation (Oncogene. 2007; 26 (18): 2606-20) and the like.

It was reported a significant increase in mRNA level of GAPDH in melanoma (Anticancer Research. 2013; 35 (1): 439-44) and non-small cell lung cancer (PLOS ONE. 2013; 8 (4): e61262), and the expression level is positively correlated with the degree of malignancy of the tumor. This is because that GAPDH plays an important role in the glycolysis process, and its anti-apoptotic function is also important for the proliferation and protection of tumor cells. For example, GAPDH can protect the telomere from shortening due to action of chemotherapy drugs. However, if conditions such as oxidative stress destroy the function of GAPDH, cells will age or die (Clinical and Experimental Pharmacology & Physiology. 2012; 39 (8): 674-9). Loss of GAPDH also leads to aging of tumor cells (Biochemical and Biophysical Research Communications. 2011; 411 (2): 409-15). It has been reported that the level of GAPDH transcription in tumors is elevated, for example free DNA in serum of breast cancer patients was detected by real-time PCR, and it was found that 84.5% of breast cancer patients were positive in DNA test, and the positive rate of stage III breast cancer patients was 84% (Tumor 2011; 31(12): 1099-1102). Currently, the related researches focus on a relationship between the level of GAPDH gene in several kinds of tumors, particularly changes in mRNA expression and tumor.

After investigation, there is no report so far on a correlation between the content of GAPDH in serum/plasma of tumor patients and tumor, and a relationship with tumorigenesis is still to be further figured out.

SUMMARY

The inventor found that an expression level of GAPDH in blood (serum and/or plasma) can be used for a diagnosis and a staging and typing of various tumors such as liver cancer, lung cancer, breast cancer, gastric cancer, colorectal cancer, as well as a monitoring of tumor patient's condition, and an evaluation of treating efficacy.

Accordingly, the present invention provides a use of GAPDH as a tumor blood marker.

In one aspect, the present invention provides a use of a reagent, which is used to detect GAPDH in a blood sample, in a preparation of a detecting composition for tumor screening, risk evaluation of tumor development in subjects, distinction of tumor progression stages, identification of therapeutic efficacy of tumor and/or risk analysis of tumor progression.

According to a specific embodiment of the present invention, in the above use of the present invention, the blood sample is a serum or plasma sample.

According to a specific embodiment of the present invention, in the above use of the present invention, the tumor includes liver cancer, lung cancer, breast cancer, gastric cancer, esophageal cancer, colorectal cancer, pancreatic cancer, cervical cancer, lymphoma or thyroid tumor.

According to a specific embodiment of the present invention, in the above use of the present invention, the reagent used to detect GAPDH in the blood sample includes a reagent used to detect GAPDH in a blood sample in Western blotting and enzyme-linked immunosorbent assay.

According to a specific embodiment of the present invention, in the above use of the present invention, the reagent used to detect GAPDH in the blood sample includes a pair of antibodies specifically binding to GAPDH or a polypeptide fragment thereof.

According to a specific embodiment of the present invention, in the above use of the present invention, the GAPDH has an amino acid sequence of SEQ ID No. 1, and said polypeptide fragment of GAPDH includes a polypeptide fragment consisting of N-terminal amino acids 40-160 of the GAPDH amino acid sequence (i.e. the amino acids 40-160 as shown in SEQ ID No. 1), or a polypeptide fragment consisting of N-terminal amino acids 180-335 of the GAPDH amino acid sequence (i.e. the amino acids 180-335 as shown in SEQ ID No. 1).

According to a specific embodiment of the present invention, in the above use of the present invention, the GAPDH is used for a diagnosis in combination with at least one additional tumor marker. In particular, the tumor screening, the risk evaluation of tumor development in the subjects, the distinction of tumor progression stages, the identification of therapeutic efficacy of tumor and/or the risk analysis of tumor progression each includes a detection of GAPDH and at least one additional tumor marker in the blood sample, and the at least one additional tumor marker includes but not limited to AFP, CEA, CA125, CA15-3, CA19-9, CA72-4, CA242, CA50, CYFRA21-1, AFU, SF, POA, TSGF.

In additional aspect, the present invention further provides an assay kit for tumor screening, risk evaluation of tumor development in subjects, distinction of tumor progression stages, identification of therapeutic efficacy of tumor and/or risk analysis of tumor progression, which includes a reagent used to detect GAPDH in a blood sample.

According to a specific embodiment of the present invention, in the above assay kit of the present invention, the reagent used to detect GAPDH in the blood sample includes a reagent used to detect GAPDH in a blood sample in Western blotting, enzyme-linked immunosorbent assay and luminescent immunoassay or colloidal gold assay.

According to a specific embodiment of the present invention, in the above assay kit of the present invention, the polypeptide fragment of GAPDH includes a polypeptide fragment consisting of N-terminal amino acids 40-160 of the GAPDH amino acid sequence, or a polypeptide fragment consisting of N-terminal amino acids 180-335 of the GAPDH amino acid sequence.

According to a specific embodiment of the present invention, the above assay kit of the present invention further includes: a 96-well ELISA Plate, a standard dilution solution, a sample dilution solution, a concentrated solution for washing, a color-developing solution and a stopping solution.

In a specific embodiment of the present invention, the kit of the present invention includes: a human GAPDH protein (a humanized version of this protein is used as a standard protein in the kit), monoclonal antibodies against human GAPDH protein, and those related reagents (the 96-well ELISA Plate, the standard dilution solution, the sample dilution solution, the concentrated solution for washing, the color-developing solution and the stopping solution). Preferably, an instruction and the like are further included for marking a detection parameter and a related determination reference value. The detection parameter includes, for example, a concentration of a standard, a dilution factor of a sample, a monitoring range of a standard curve, an accuracy, a minimum detection limit, an amount of each component in the reaction system, a reaction temperature and time, etc., and the determination reference values are, for example, reference values for different tumors.

In additional aspect, the invention also provides a method of determining whether a subject has or is at risk of developing a cancer, the method including:
a. obtaining a blood sample from the subject;
b. determining a concentration of GAPDH in a serum or plasma sample from the subject;
c. comparing the concentration of GAPDH in the serum or plasma sample from the subject with a reference concentration, and when the concentration of GAPDH in the sample is greater than or equal to the reference concentration, the subject is determined as a tumor patient or having a risk of developing a tumor.

In a specific embodiment of the present invention, a reference value for being determined as having liver cancer is 5.95 µg/ml (may also be rounded to 6 µg/ml), that is, when a concentration of GAPDH in the blood sample of the subject is in the range of 0-6 µg/ml, it is considered to be a normal value. A subject is determined to have a tumor or be at risk of developing cancer, if a concentration of GAPDH in the blood sample is greater than or equal to 6 µg/ml.

In the present invention, after an error caused by the detection method is ruled out, the detection result of the subject increased or decreased within 25% is regarded as having the same determination meaning. That is, the determination reference value for the liver cancer is 6 µg/ml, and when the detection result is greater than or equal to 4.5 µg/ml, the subject may also be determined to have a tumor or a risk of developing a cancer.

In additional aspect, the invention also provides a method for distinguishing stages of tumor progression, the method including:
a. obtaining a blood sample from the subject;
b. determining a concentration of GAPDH in a serum or plasma sample from the subject;
c. comparing the concentration of GAPDH in the serum or plasma sample from the subject with a series of reference concentration, so as to determine the stage of tumor progression.

In additional aspect, the invention also provides a method for monitoring a tumor patient's condition, the method including:
Obtaining blood samples of the subject at the beginning and the end of a period;
Determining a concentration of GAPDH in a serum or plasma sample from the subject;
Comparing the concentration of GAPDH in the serum or plasma sample of the subject at the beginning and end of a period, if the concentration of GAPDH in the sample at the end is lower than that at the beginning, and the percentage of decrease reaches or exceeds a set reference value, then it is determined that the condition is relieved; if the concentration of GAPDH in the sample at the end is increased in comparison to that at the beginning, is not significantly different from that at the beginning or the changed range does not reach or exceed the set reference value, then it is determined that the condition is not relieved.

In the method, the reference value may be selected from 10-50%. In a specific embodiment of the invention, the reference value is 30%. Moreover, the reference value ±25% in the present invention is regarded as having the same determination meaning. That is, when the reference value is 30%, and a concentration of GAPDH in a blood sample of a tumor patient is decreased by 22.5%, the condition of the patient may also be considered to have progressed better. The "period" therein can be set according to the patient's condition, and "a treatment" includes a daily treatment, one cycle of treatment and/or multiple cycles of treatment.

In additional aspect, the invention also provides a method for evaluating tumor patient's therapy efficacy, the method including:
a. obtaining blood samples of the subject before and after receiving a treatment;
b. determining a concentration of GAPDH in a serum or plasma sample from the subject;
c. comparing the concentration of GAPDH in the serum or plasma sample of the subject before and after the treatment, if the concentration of GAPDH in the sample after the treatment is lower than that before the treatment, and the percentage of decrease reaches or exceeds a set reference value, then it is determined that the therapy or medication is beneficial for the relief of the condition; if the concentration of GAPDH in the sample after the treatment is increased in comparison to that before the treatment, is not significantly different from that before the treatment or the changed range does not reach or exceed the set reference value, then it is determined that the therapy or medication has poor efficacy.

In the method, the reference value may be selected from 10-50%. In a specific example of the invention, a concentration of GAPDH in the serum of a lung cancer patient before a treatment is 22.63 µg/ml, and is decreased to 20.41 µg/ml after the treatment, reduced by 9.81%, roughly 10% after rounding. In additional specific example of the invention, a concentration of GAPDH in the serum of a lung cancer patient before a treatment is 46.51 µg/ml, and is decreased to 24.20 µg/ml after treatment, reduced by 47.97%, roughly 50% after rounding. In a specific embodiment of the invention, the reference value is 30%. Moreover, the reference value ±25% in the present invention is regarded as having the same determination meaning. That is, when the reference value is 30%, and the concentration of GAPDH in blood sample of the tumor patient is decreased by 22.5%, the therapy efficacy may also be considered to be good. The "period" therein can be set according to the patient's condition, and "a treatment" includes a daily treatment, one cycle of treatment and/or multiple cycles of treatment.

In additional aspect, the invention also provides a method of determining whether a subject has or is at risk of developing a cancer by a combination diagnosis, the method including:
 a. obtaining a blood sample from a subject;
 b. determining a concentration of GAPDH and a concentration of at least one additional tumor marker in a serum or plasma sample from the subject;
 c. comparing the concentration of GAPDH and the concentration of at least one additional tumor marker in the serum or plasma sample from the subject with a set reference value, and when the concentration of GAPDH and the concentration of at least one additional tumor marker in the sample are greater than or equal to the reference concentration, the subject is determined as a tumor patient or having a risk of developing a tumor.

In this method, the reference value for GAPDH concentration is 5.57-11.75 µg/ml, and the reference value ±25% is regarded as having the same determination meaning.

In additional aspect, the invention also provides a method for distinguishing stages of tumor progression by a combination diagnosis, the method including:
 a. obtaining a blood sample from the subject;
 b. determining a concentration of GAPDH and a concentration of at least one additional tumor marker in a serum or plasma sample from the subject;
 c. comparing the concentration of GAPDH and the concentration of at least one additional tumor marker in the serum or plasma sample from the subject with a series of reference concentration, so as to determine the stages of tumor progression.

In additional aspect, the invention also provides a method for monitoring a tumor patient's condition by a combination diagnosis, the method including:

Obtaining blood samples of a subject at the beginning and the end of a period;
Determining a concentration of GAPDH and a concentration of at least one additional tumor marker in a serum or plasma sample from the subject;
Comparing the concentration of GAPDH and the concentration of at least one additional tumor marker in the serum or plasma sample of the subject at the beginning and end of the period, if the concentration of GAPDH and the concentration of at least one additional tumor marker in the sample at the end are lower than those at the beginning, and the percentage of decrease reaches or exceeds a set reference value, then it is determined that the condition is relieved; if the concentration of GAPDH and the concentration of at least one additional tumor marker in the sample at the end are increased in comparison to that at the beginning, are not significantly different from that at the beginning or the changed range does not reach or exceed the set reference value, then it is determined that the condition is not relieved.

In additional aspect, the invention also provides a method for evaluating tumor patient's therapy efficacy by a combination diagnosis, the method including:
 a. obtaining blood samples of a subject before and after receiving a treatment;
 b. determining a concentration of GAPDH and a concentration of at least one additional tumor marker in a serum or plasma sample from the subject;
 c. comparing the concentration of GAPDH and the concentration of at least one additional tumor marker in the serum or plasma sample of the subject before and after the treatment, if the concentration of GAPDH and the concentration of at least one additional tumor marker in the sample after the treatment are lower than those before the treatment, and the percentage of decrease reaches or exceeds a set reference value, then it is determined that the therapy or medication is beneficial for the relief of the condition; if the concentration of GAPDH and the concentration of at least one additional tumor marker in the sample after the treatment are increased in comparison to that before the treatment, are not significantly different from that before the treatment or the changed range does not reach or exceed the set reference value, then it is determined that the therapy or medication has poor efficacy.

In the above methods of the present invention, the tumor includes, but not limited to, liver cancer, lung cancer, breast cancer, gastric cancer, esophageal cancer, colorectal cancer, pancreatic cancer, cervical cancer, lymphoma or thyroid tumor.

In the above methods of the present invention, the at least one additional tumor marker includes, but not limited to, AFP, CEA, CA125, CA15-3, CA19-9, CA72-4, CA242, CA50, CYFRA21-1, AFU, SF, POA, TSGF.

The term "tumor" as used in the present invention means, but is not limited to, a malignant tumor, and is equally applicable to a benign tumor or an early stage of tumorigenesis.

In the present invention, by detecting the content of GAPDH in a human blood sample, it is possible to perform a diagnosis, a prognosis evaluation and a treating-efficacy monitoring of tumors, such as liver cancer, lung cancer, breast cancer, gastric cancer, esophageal cancer, colorectal cancer and the like, and can be used for, but not limited to, tumor screening, risk evaluation of tumor development in subjects, distinction of tumor progression stages, identification of therapeutic efficacy of tumor and risk analysis of tumor progression.

DETAILED DESCRIPTION

The present invention will be further illustrated in connection with the following specific embodiments. It should be understood that these examples are only to explain the present invention, but not intended to limit the scope of the invention. The experimental methods in the following examples which are not specified with the specific conditions were usually carried out in accordance with conventional conditions, or according to the conditions recommended by the manufacturer.

The term "tumor" as used in the present invention means, but is not limited to, a malignant tumor, and the tumor marker and the detection kit thereof according to the present invention are equally applicable to a benign tumor or an early stage of tumorigenesis.

The term "blood sample" as used in the present invention refers to a sample obtained from the blood of a subject, specifically including serum and/or plasma samples.

The term "healthy subjects" as used in the present invention refers to a population that is considered at the moment as a non-tumor patient, because he or she has not been subjected to any diagnosis by biochemical, imaging or pathological methods.

The term "sensitivity" as used in the present invention refers to a probability, for a case in which a tumor is detected by a pathological method, to also have a positive detection result by the kit.

The "specificity" as used in the present invention refers to a probability for a healthy subject to also have a negative detection result by the kit.

Example 1

The plasma was collected from healthy subjects and patients having different types of tumors. Western blotting was used to detect the concentration of GAPDH in the plasma, which proved that GAPDH can be used as a tumor marker.

The specific experimental process is as follows:
1. Sample Collection
Blood was collected from each of healthy subjects and patients pathologically diagnosed as having gastric cancer, lung cancer, or liver cancer, into anticoagulation tubes, and the tubes were inverted 8-10 times. The plasma was separated by centrifugation at 800-1000 rpm for 10 minutes, and the separated plasma was dispensed into EP tubes (50 µL each part), and quickly stored at −20° C. for cryopreservation.

2. Sample Processing
Each sample of plasma was diluted 20 times and then added with 5× loading buffer and heated at 100° C. for 10 minutes.

3. Sample Detection
The treated samples were detected for GAPDH by Western blotting.

Figure 1:
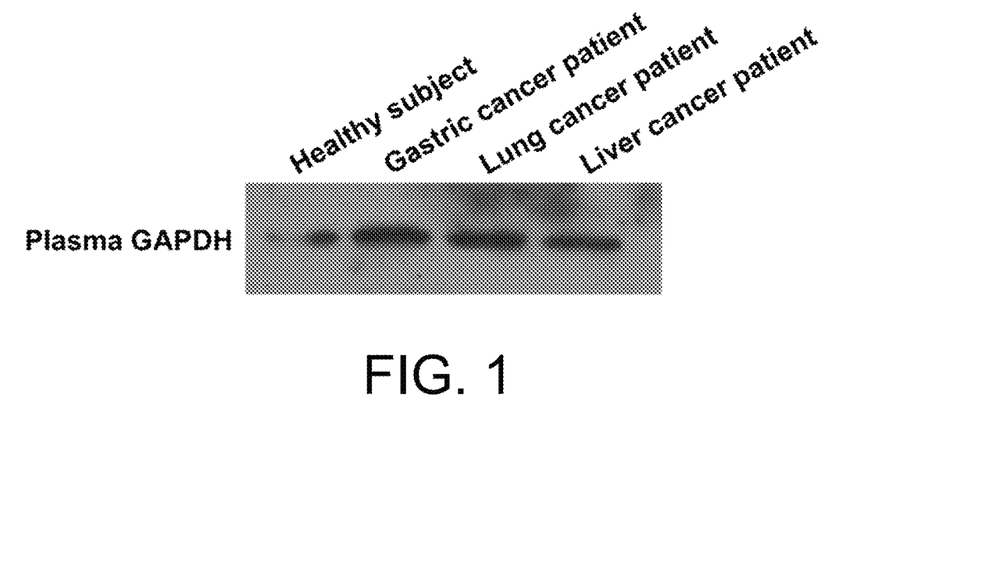
FIG. 1 is a Western blotting result of GAPDH in plasma from patients with different tumors.

4. Result Analysis
As shown in FIG. 1, GAPDH was detected by Western blotting in plasma samples from healthy subjects and the patients with different tumors. GAPDH levels in plasma of patients with gastric cancer, lung cancer or liver cancer were significantly higher than that in healthy subjects, indicating that GAPDH in blood can be used as a tumor marker distinguishing healthy subjects from cancer patients.

Example 2

The blood of healthy subjects and liver cancer patients was collected. The concentration of GAPDH in serum was detected by Enzyme linked immunosorbent assay (ELISA), and the effectiveness of GAPDH in the diagnosis of liver cancer was evaluated.

The specific experimental process is as follows:
1. Sample Selection
Healthy subjects: a population who has not been subjected to any diagnosis by biochemical, imaging or pathological methods and is considered to be a non-tumor patient.

Liver cancer patients: the patients diagnosed as having liver cancer by pathological diagnosis, including different types and different stages of liver cancer.

2. Sample Collection
Blood was collected from each of healthy subjects and liver cancer patients, and allowed to stand at room temperature for 20 minutes. The serum was separated by centrifugation at 800-1000 rpm for 10 minutes, and the separated serum was dispensed into EP tubes (50 µL each part), and quickly stored at −20° C. for cryopreservation.

The samples (serum samples) of liver cancer patients receiving drug treatments were collected once before the start of treatment, and collected once after the end of the treatment period.

3. Sample Detection
The collected serum samples were detected by ELISA for concentration of GAPDH therein.

4. Data Analysis
The concentration of GAPDH in the clinical samples was counted, and a Receiver Operating Characteristic curve (ROC curve) was plotted by using the true positive and false positive (1-specificity) as the ordinate and the abscissa, respectively. The area under ROC curve and 95% CI were calculated, to determine the correlation between GAPDH and tumor, so as to evaluate the value of the auxiliary diagnosis.

5. Research Result
(1) Subjects Category

| Subjects category | Case number |
| --- | --- |
| Healthy subjects | 67 |
| Liver cancer patients | 52 |
| Total | 119 |

Figure 2:
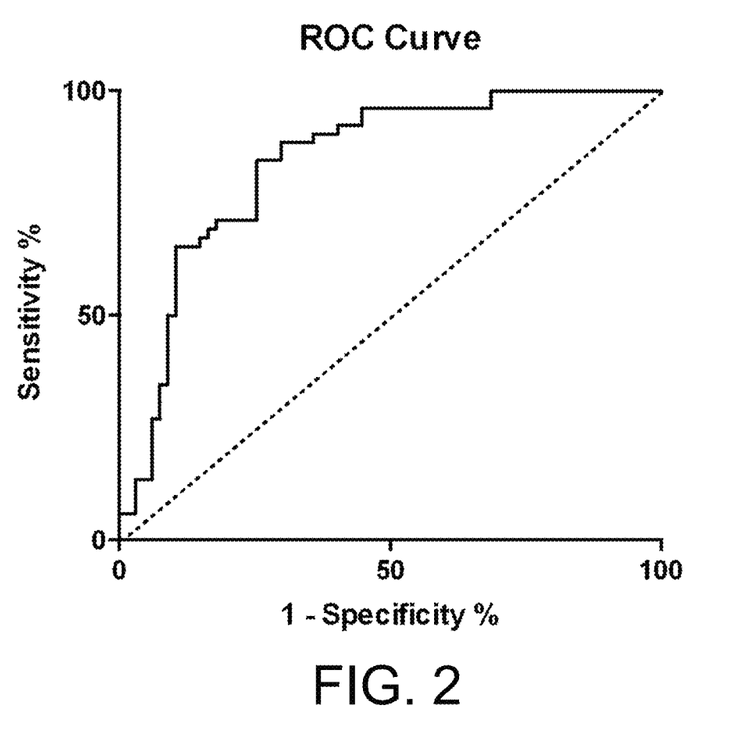
FIG. 2 is a ROC curve of liver cancer patients relative to healthy subjects.

(2) ROC Curve and Evaluation Criteria (FIG. 2)

| Variable | Numerical value |
|---|---|
| Threshold | 5.95(μg/ml) |
| Sensitivity | 84.62% |
| Specificity | 74.63% |
| Area under the curve | 0.8407 |

(3) Evaluation of Treating Efficacy for the Medicine Therapy

| No. | Before treatment (μg/ml) | After treatment (μg/ml) |
|---|---|---|
| 1 | 17.16 | 4.20 |
| 2 | 15.86 | 3.60 |
| 3 | 12.63 | 2.60 |

Example 3

On the one hand, the serums were collected from healthy subjects and lung cancer patients, and the concentration of GAPDH in serum was detected by ELISA procedure such that the effectiveness of GAPDH in the diagnosis of lung cancer was evaluated. On the other hand, some patients with lung cancer were followed up, from which patients the blood samples were collected before and after treatment. The blood samples were tested for changes in serum GAPDH concentration, such that the effectiveness of GAPDH in condition monitoring and therapy efficacy evaluation was evaluated.

The specific experimental process is as follows:

1. Sample Selection

Healthy subjects: a population who has not been subjected to any diagnosis by biochemical, imaging or pathological methods and is considered to be a non-tumor patient.

Lung cancer patients: the patients diagnosed as having lung cancer by pathological diagnosis, including different types and different stages of lung cancer.

2. Sample Collection

Blood was collected from each of healthy subjects and pathologically diagnosed lung cancer patients, and allowed to stand at room temperature for 20 minutes. The serum was separated by centrifugation at 800-1000 rpm for 10 minutes, and the separated serum was dispensed into EP tubes (50 μL each part), and quickly stored at −20° C. for cryopreservation.

3. Sample Detection

The collected serum samples were detected by ELISA for concentration of GAPDH therein.

4. Data Analysis

The concentration of GAPDH in the clinical samples was counted, and a Receiver Operating Characteristic curve (ROC curve) was plotted by using the true positive and false positive (1-specificity) as the ordinate and the abscissa, respectively. The area under ROC curve and 95% CI were calculated, to determine the correlation between GAPDH and tumor, so as to evaluate the value of the auxiliary diagnosis.

5. Research Result (1) Subjects Category

| Subjects category | Case number |
|---|---|
| Healthy subjects | 67 |
| Lung cancer patients | 56 |
| Total | 123 |

Figure 3:
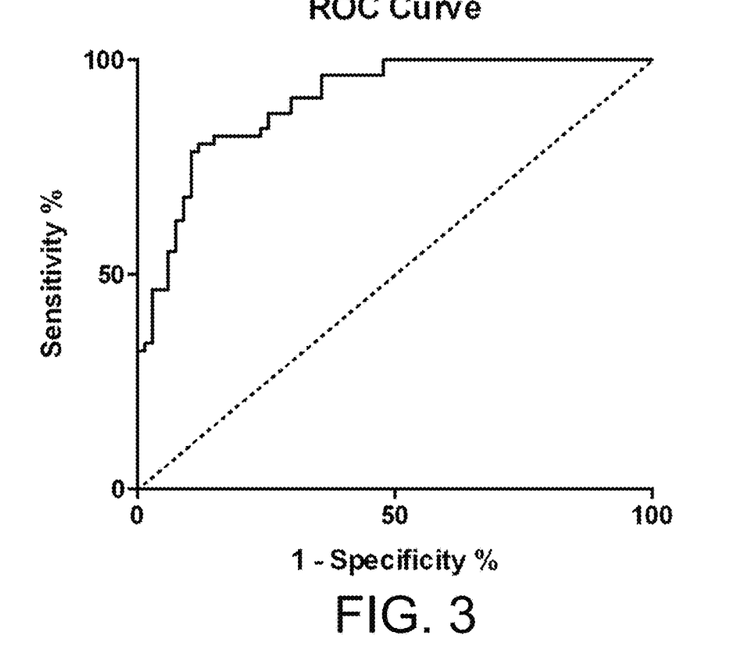
FIG. 3 is a ROC curve of lung cancer patients relative to healthy subjects.

(2) ROC Curve and Evaluation Criteria (FIG. 3)

| Variable | Numerical value |
|---|---|
| Threshold | 10.58(μg/ml) |
| Sensitivity | 80.36% |
| Specificity | 88.06% |
| Area under the curve | 0.9043 |

(3) Evaluation of Treating Efficacy for the Medicine Therapy

| No. | Before treatment (μg/ml) | After treatment (μg/ml) |
|---|---|---|
| 1 | 46.51 | 24.20 |
| 2 | 23.84 | 8.60 |
| 3 | 12.63 | 6.60 |
| 4 | 22.63 | 20.41 |

Example 4

On the one hand, the serums were collected from healthy subjects and gastric cancer patients, and the concentration of GAPDH in serum was detected by ELISA procedure such that the effectiveness of GAPDH in the diagnosis of gastric cancer was evaluated. On the other hand, some patients with gastric cancer were followed up, from which patients the blood samples were collected before and after treatment. The blood samples were tested for changes in serum GAPDH concentration, such that the effectiveness of GAPDH in condition monitoring and therapy efficacy evaluation was evaluated.

The specific experimental process is as follows:

1. Sample Selection

Healthy subjects: a population who has not been subjected to any diagnosis by biochemical, imaging or pathological methods and is considered to be a non-tumor patient. Gastric cancer patients: the patients diagnosed as having gastric cancer by pathological diagnosis, including different types and different stages of gastric cancer.

2. Sample Collection

Blood was collected from each of healthy subjects and pathologically diagnosed gastric cancer patients, and allowed to stand at room temperature for 20 minutes. The serum was separated by centrifugation at 800-1000 rpm for 10 minutes, and the separated serum was dispensed into EP tube (50 μL each part), and quickly stored at −20° C. for cryopreservation.

The samples (serum samples) of gastric cancer patients receiving drug treatment were collected once before the start of treatment, and collected once after the end of the treatment period.

3. Sample Detection

The collected serum samples were detected by ELISA for concentration of GAPDH therein.

4. Data Analysis

The concentration of GAPDH in the clinical samples was counted, and a Receiver Operating Characteristic curve (ROC curve) was plotted by using the true positive and false positive (1-specificity) as the ordinate and the abscissa, respectively. The area under ROC curve and 95% CI were calculated, to determine the correlation between GAPDH and cancer, so as to evaluate the value of the auxiliary diagnosis.

5. Research Result (1) Subjects Category

| Subjects category | Case number |
|---|---|
| Healthy subjects | 67 |
| Gastric cancer patients | 48 |
| Total | 115 |

Figure 4:
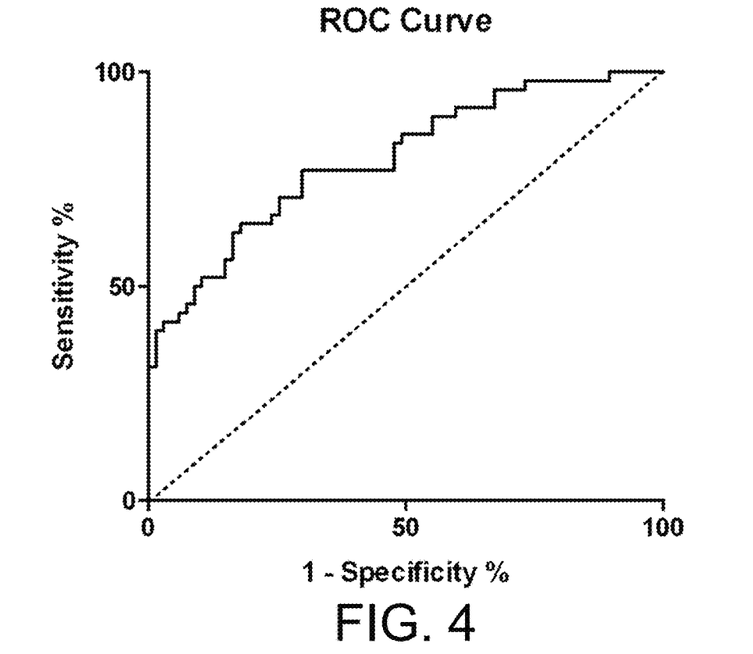
FIG. 4 is a ROC curve of gastric cancer patients relative to healthy subjects.

(2) ROC Curve and Evaluation Criteria (FIG. 4)

| Variable | Numerical value |
|---|---|
| Threshold | 5.57(μg/ml) |
| Sensitivity | 77.08% |
| Specificity | 70.15% |
| Area under the curve | 0.7976 |

(3) Evaluation of Treating Efficacy for the Medicine Therapy

| No. | Before treatment(μg/ml) | After treatment(μg/ml) |
|---|---|---|
| 1 | 55.81 | 27.34 |
| 2 | 45.62 | 22.65 |
| 3 | 19.55 | 5.30 |

Example 5

The blood of healthy subjects and colorectal cancer patients were collected. The concentration of GAPDH in serum was detected by Enzyme linked immunosorbent assay (ELISA), and the effectiveness of GAPDH in the diagnosis of colorectal cancer was evaluated.

The specific experimental process is as follows:

1. Sample Selection

Healthy subjects: a population who has not been subjected to any diagnosis by biochemical, imaging or pathological methods and is considered to be a non-tumor patient. Colorectal cancer patients: the patients diagnosed as having colorectal cancer by pathological diagnosis, including different types and different stages of colorectal cancer.

2. Sample Collection

Blood was collected from each of healthy subjects and pathologically diagnosed colorectal cancer patients, and allowed to stand at room temperature for 20 minutes. The serum was separated by centrifugation at 800-1000 rpm for 10 minutes, and the separated serum was dispensed into EP tube (50 μL each part), and quickly stored at −20° C. for cryopreservation.

3. Sample Detection

The collected serum samples were detected by ELISA for concentration of GAPDH therein.

4. Data Analysis

The concentration of GAPDH in the clinical samples was counted, and a Receiver Operating Characteristic curve (ROC curve) was plotted by using the true positive and false positive (1-specificity) as the ordinate and the abscissa, respectively. The area under ROC curve and 95% CI were calculated, to determine the correlation between GAPDH and tumor, so as to evaluate the value of the auxiliary diagnosis.

5. Research Result (1) Subjects Category

| Subjects category | Case number |
|---|---|
| Healthy subjects | 67 |
| Colorectal cancer patients | 30 |
| Total | 97 |

Figure 5:
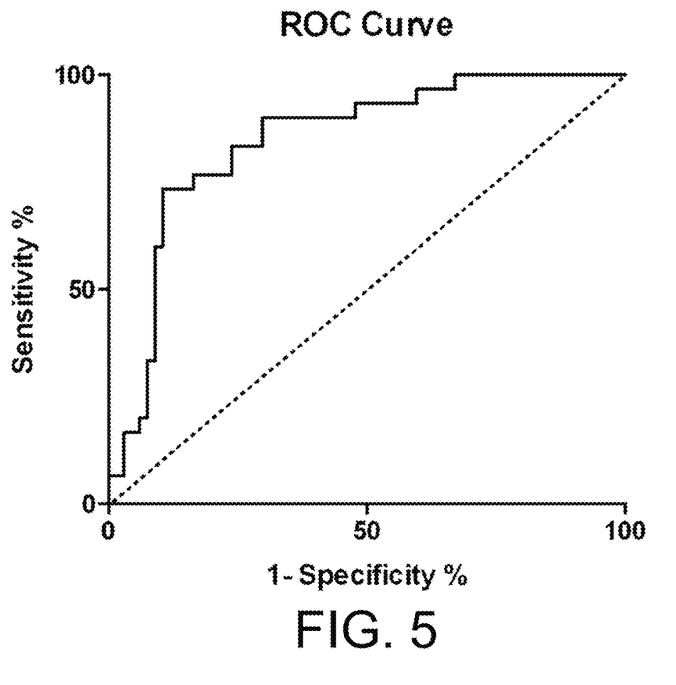
FIG. 5 is a ROC curve of colorectal cancer patients relative to healthy subjects.

(2) ROC Curve and Evaluation Criteria (FIG. 5)

| Variable | Numerical value |
|---|---|
| Threshold | 11.75(μg/ml) |
| Sensitivity | 73.33% |
| Specificity | 89.55% |
| Area under the curve | 0.8474 |

Example 6

On the one hand, the serums were collected from healthy subjects and pancreatic cancer patients, and the concentration of GAPDH in serum was detected by ELISA procedure such that the effectiveness of GAPDH in the diagnosis of pancreatic cancer was evaluated. On the other hand, some patients with pancreatic cancer were followed up, from which patients the blood samples were collected before and after treatment. The blood samples were tested for changes in serum GAPDH concentration, such that the effectiveness of GAPDH in condition monitoring and therapy efficacy evaluation was evaluated.

The specific experimental process is as follows:

1. Sample Selection

Healthy subjects: a population who has not been subjected to any diagnosis by biochemical, imaging or pathological methods and is considered to be a non-tumor patient. Pancreatic cancer patients: the patients diagnosed as having pancreatic cancer by pathological diagnosis, including different types and different stages of pancreatic cancer.

2. Sample Collection

Blood was collected from each of healthy subjects and pathologically diagnosed pancreatic cancer patients, and allowed to stand at room temperature for 20 minutes. The serum was separated by centrifugation at 800-1000 rpm for 10 minutes, and the separated serum was dispensed into EP tube (50 μL each part), and quickly stored at −20° C. for cryopreservation.

The samples (serum samples) of pancreatic cancer patients receiving drug treatment were collected once before the start of treatment, and collected once after the end of the treatment period.

3. Sample Detection

The collected serum samples were detected by ELISA for concentration of GAPDH therein.

4. Data Analysis

The concentration of GAPDH in the clinical samples was counted, and a Receiver Operating Characteristic curve (ROC curve) was plotted by using the true positive and false positive (1-specificity) as the ordinate and the abscissa, respectively. The area under ROC curve and 95% CI were calculated, to determine the correlation between GAPDH and tumor, so as to evaluate the value of the auxiliary diagnosis.

5. Research Result (1) Subjects Category

| Subjects category | Case number |
|---|---|
| Healthy subjects | 67 |
| Pancreatic cancer patients | 24 |
| Total | 91 |

Figure 6:
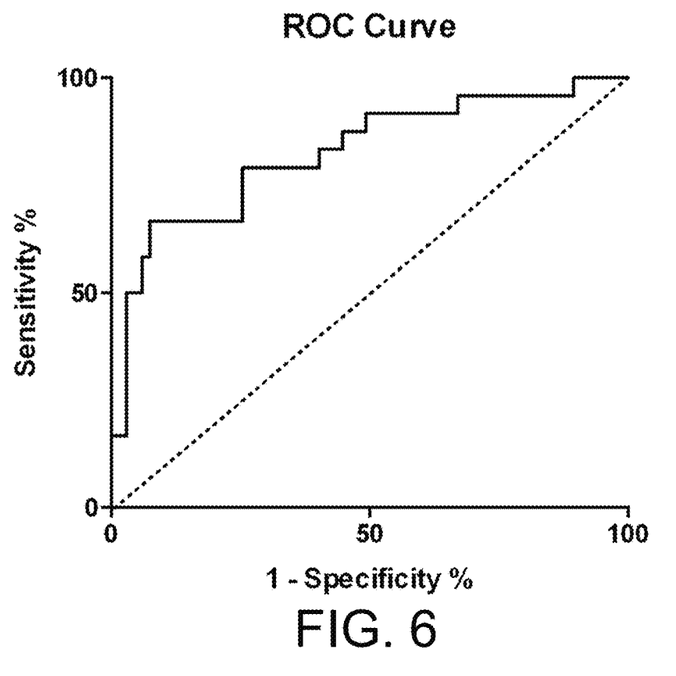
FIG. 6 is a ROC curve of pancreatic cancer patients relative to healthy subjects.

(2) ROC Curve and Evaluation Criteria (FIG. 6)

| Variable | Numerical value |
|---|---|
| Threshold | 5.94(μg/ml) |
| Sensitivity | 79.17% |
| Specificity | 74.63% |
| Area under the curve | 0.8259 |

Example 7

The blood of healthy subjects and patients with different types of tumors was collected. The concentration of GAPDH in serum was detected by Enzyme linked immunosorbent assay (ELISA), in order to prove that GAPDH can be used as a marker for various tumors.

The specific experimental process is as follows:

1. Sample Collection

Blood was collected from each of healthy subjects and patients pathologically diagnosed with liver cancer, lung cancer, breast cancer, gastric cancer, esophageal cancer, colorectal cancer, pancreatic cancer, cervical cancer, lymphoma, or thyroid tumor, and allowed to stand at room temperature for 20 minutes. The serum was separated by centrifugation at 800-1000 rpm for 10 minutes, and the separated serum was dispensed into EP tube (50 μL each part), and quickly stored at −20° C. for cryopreservation.

2. Sample Detection

The collected serum samples were detected by ELISA for concentration of GAPDH therein.

3. Result Analysis

Figure 7:
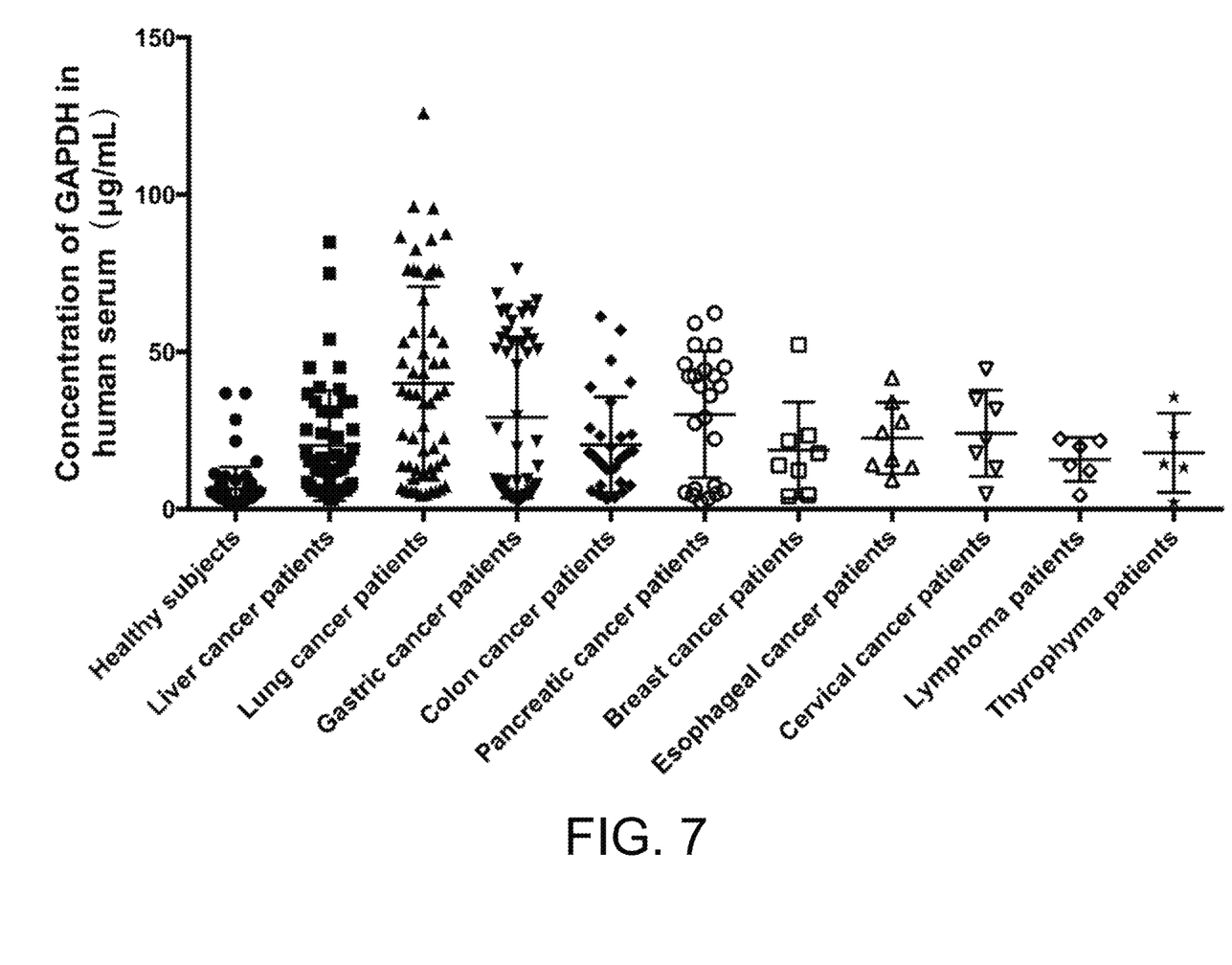
FIG. 7 is a summary of the detection results of serum GAPDH contents in patients with a variety of tumor.

As shown in FIG. 7, the levels of GAPDH in the serum of patients with liver cancer, lung cancer, gastric cancer, colorectal cancer, pancreatic cancer, breast cancer, esophageal cancer, cervical cancer, lymphoma, or thyroid tumor are significantly higher than that of the healthy subjects, indicating that GAPDH in the blood can be used as a marker for a variety of tumors, distinguishing between healthy subjects and tumor patients.

The concentrations of GAPDH in patients with different tumors measured in this Examples are shown in table below.

| Category | Case number | Average concentration (μg/ml) |
|---|---|---|
| Healthy subjects | 67 | 3.66 |
| Liver cancer patients | 52 | 20.22 |
| Lung cancer patients | 56 | 41.74 |
| Gastric cancer patients | 48 | 29.16 |
| Colorectal cancer patients | 30 | 20.43 |
| Pancreatic cancer patients | 24 | 30.05 |
| Breast cancer patients | 9 | 18.70 |
| Esophageal cancer patients | 9 | 22.57 |
| Cervical cancer patients | 7 | 24.10 |
| Lymphoma patients | 6 | 15.75 |
| Thyroid tumor patients | 5 | 17.88 |

Example 8

Figure 8:
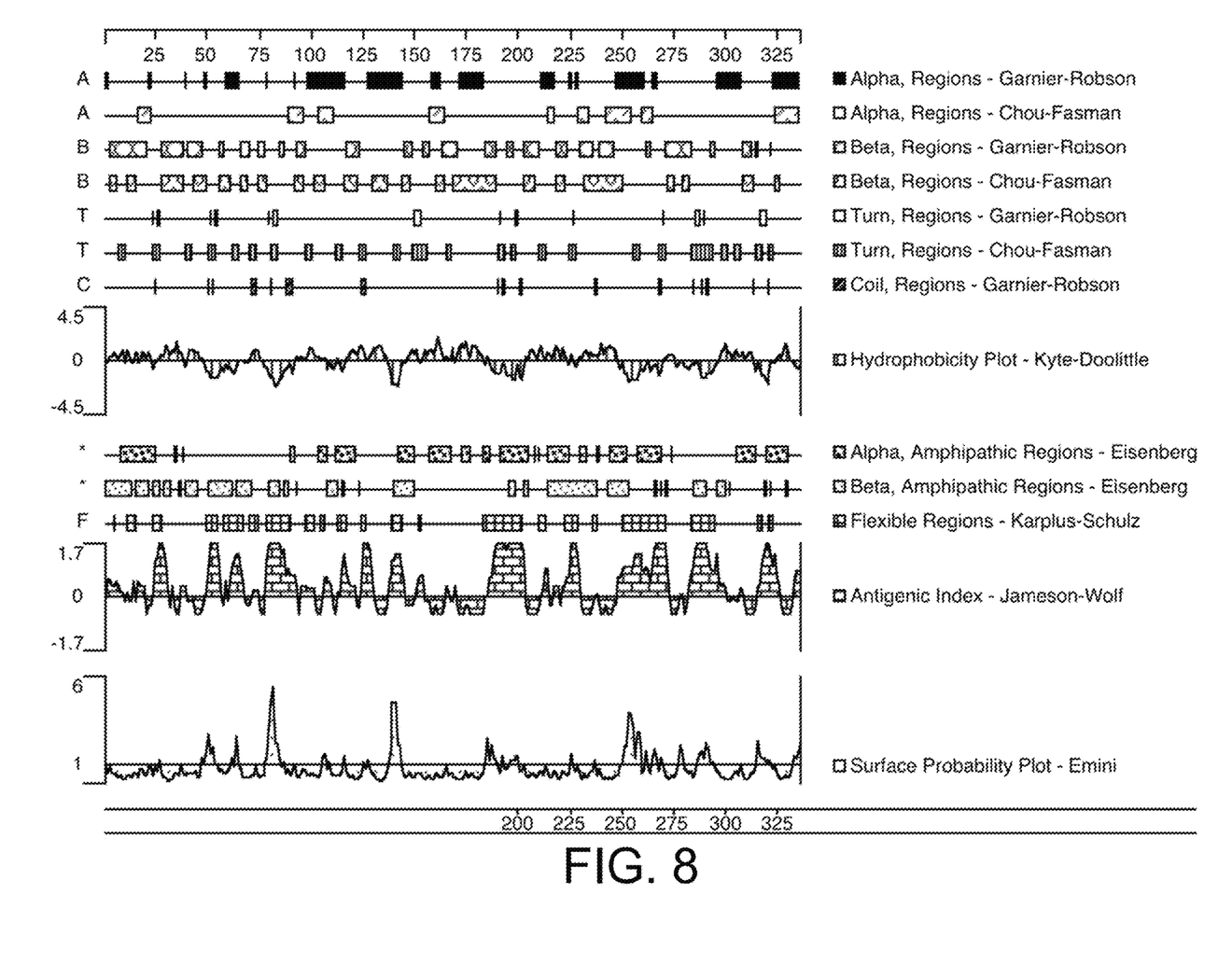
FIG. 8 shows the secondary structure, hydrophilicity, flexibility, antigenic index and surface probability of a GAPDH protein.

In this example, the amino acid sequence of GAPDH was first obtained from the NCBI database, and then the secondary structure and antigen domain of GAPDH were predicted using DNASTAR Protean software. The software employs the Garnier-Robson and Chou-Fasman algorithms for prediction of the secondary structure of the protein (α-helix, β-sheet, turn and random coil); the Kyte-Doolittle algorithm for prediction of the hydrophilicity of the protein; the Karplus-Schultz algorithm for prediction of the flexibility of the protein; the Jameson-Wolf algorithm for prediction of the antigenic index of the protein; the Plot-Emini algorithm for prediction of the surface probability of the protein. The results of the above predictions for secondary structure, hydrophilicity, flexibility, antigenic index and surface probability were considered in combination (FIG. 8), the paired-antibodies were prepared against a peptide consisting of amino acids 40-160 and a peptide consisting of amino acids 180-335 of SEQ ID No. 1, respectively. One of the paired-antibodies against amino acids 40-160 of SEQ ID No. 1 includes heavy chain variable region (the amino acid sequences: SEQ ID. 2, SEQ ID. 3, SEQ ID ID. 4) and light chain variable region (the amino acid sequences: SEQ ID. 5, SEQ ID. 6, SEQ ID ID. 7). The other of the paired-antibodies against amino acids 180-335 of SEQ ID No. 1 includes heavy chain variable region (the amino acid sequences: SEQ ID. 8, SEQ ID. 9, SEQ ID ID. 10) and light chain variable region (the amino acid sequences: SEQ ID. 11, SEQ ID. 12, SEQ ID ID. 13).

The specific preparation process of the antibody can be carried out by referring to the prior art, and is briefly described as follows:

1. Preparation of Antigen.

Genes were synthesized for amino acid sequences 40-160 and 180-335 of SEQ ID No. 1, respectively, the vectors thereof were constructed, and the antigens were expressed in prokaryotic expression system.

2. Obtaining Monoclonal Hybridoma Cells.

Anti-serum was obtained by immunizing BALB/c mice with the antigen and used to detect the antigen. After successful detection, B cells were isolated and fused with myeloma cells to prepare monoclonal hybridoma cells.

3. Obtaining Paired Antibodies.

The different monoclonal antibodies produced by different hybridoma cells were paired pair wisely, and tested by using prokaryotic expressed full-length pro reference concentrations tein as antigen, and it was obtained at least one pair of antibodies that meet the detection requirements.

Example 9

This Example provides an assay kit for detecting GAPDH in a blood sample. The kit comprises a GAPDH standard protein, a pair of monoclonal antibodies against GAPDH (including primary and secondary antibodies), a 96-well ELISA Plate, a standard dilution solution, a sample dilution solution, a concentrated solution for washing, a color-developing solution and a stopping solution, as well as other experimental aiding materials.

GAPDH in a blood sample of an individual to be tested can be detected using the kit by a method as follows:

1. Adding 50 μl of the diluted standard or sample to the coated 96-well ELISA Plate, and allowing the plate to be still at 37° C. for 30-60 min.
2. Discarding the liquid in the well, and washing three times with 300 μl of washing solution per well.
3. Adding 50 μl of secondary antibody solution to each well, and allowing the plate to be still at 37° C. for 30-60 min.
4. Discarding the liquid in the well, and washing three times with 300 μl of washing solution per well.
5. Adding 100 μl of color-developing solution to each well and allowing the plate to be still at 37° C. for 10-15 min.
6. Adding 50 μl of stopping solution to each well, and reading the absorbance at 450 nm.

The standard curve range detected by the kit is 0-10 μg/ml, and the minimum detection limit is 0.10 μg/ml.

In this example, by employing antibodies prepared according to Example 8, or commercial monoclonal antibodies against GAPDH, different kits are provided to detect GAPDH in a blood sample. The detection sensitivities of these kits used for different cancers are shown in the following table.

| Cancers | Detection sensitivity of kits containing commercial antibodies | Detection sensitivity of kits containing antibodies prepared in Example 8 |
|---|---|---|
| Liver cancer | 60.36% | 84.62% |
| Lung cancer | 58.69% | 80.36% |
| Gastric cancer | 55.42% | 77.08% |
| Colorectal cancer | 64.57% | 73.33% |
| Pancreatic cancer | 60.06% | 79.17% |

The above results indicate that the kits used to detect GAPDH in a blood sample of the present invention have a good detection sensitivity.

What is claimed is:

1. A method for tumor screening and evaluating risk of tumor development, comprising:

obtaining a blood sample from a subject;

determining a concentration of Glyceraldehyde 3-phosphate dehydrogenase (GAPDH) in the blood sample by a sandwich enzyme-linked immunosorbent assay (ELISA);

detecting a concentration of at least one additional tumor marker in the blood sample, wherein the at least one additional tumor marker comprises alpha-fetoprotein (AFP), carcinoembryonic antigen (CEA), carbohydrate antigen 19-9 (CA19-9), carbohydrate antigen 72-4 (CA72-4), carbohydrate antigen 242 (CA242), cytokeratin-19-fragment (CYFRA21-1), and alpha-1-fucosidase (AFU); and comparing the concentration of GAPDH in the blood sample with a first reference concentration, and comparing the concentration of the at least one additional tumor marker in the blood sample with a second reference concentration, wherein when the concentration of GAPDH in the blood sample is greater than or equal to the first reference concentration and the concentration of the at least one additional tumor marker in the blood sample is greater than the second reference concentration, the subject is determined as a tumor patient or having a risk of developing a tumor, wherein the first reference concentration of 5.95 μg/ml and the second reference concentration of AFP of 400 ng/ml are used to determine whether the subject has liver cancer or is at risk of developing liver cancer, wherein the first reference concentration of 10.58 μg/ml and the second reference concentration of CYFRA21-1 of 3.15 ng/l are used to determine whether the subject has lung cancer or is at risk of developing lung cancer, wherein the first reference concentration of 5.57 μg/ml, the second reference concentration of CEA of 5 ng/ml, the second reference concentration of CA19-9 of 37 U/ml and the second reference concentration of CA72-4 of 6.9 U/ml are used to determine whether the subject has gastric cancer or is at risk of developing gastric cancer, wherein the first reference concentration of 11.75 μg/ml, the second reference concentration of CEA of 5 ng/ml and the second reference concentration of AFU of 5.6 U/l are used to determine whether the subject has colorectal cancer or is at risk of developing colorectal cancer, wherein the first reference concentration of 5.94 μg/ml and the second reference concentration of CA19-9 of 37 U/ml and/or CA242 of 20 U/ml are used to determine whether the subject has pancreatic cancer or a risk of developing pancreatic cancer, wherein an amino acid sequence of GAPDH is shown as SEQ ID No. 1, the sandwich ELISA is performed by a capture antibody and a detection antibody, the capture antibody binds to N-terminal amino acids 40-160 of the GAPDH amino acid sequence for capturing GAPDH from the blood sample, and the detection antibody binds to N-terminal amino acids 180-335 of the GAPDH amino acid sequence for measuring the concentration of GAPDH, wherein the capture antibody comprises heavy chain variable region and light chain variable region, the heavy chain variable region comprises CDR1 shown as SEQ ID No. 2, CDR2 shown as SEQ ID No. 3 and CDR3 shown as SEQ ID No. 4, the light chain variable region comprises CDR1 shown as SEQ ID No. 5, CDR2 shown as SEQ ID No. 6 and CDR3 shown as SEQ ID No. 7, wherein the detection antibody comprises heavy chain variable region and light chain variable region, the heavy chain variable region comprises CDR1 shown as SEQ ID No. 8, CDR2 shown as SEQ ID No. 9 and CDR3 shown as SEQ ID No. 10, the light chain variable region comprises CDR1 shown as SEQ ID No. 11, CDR2 shown as SEQ ID No. 12 and CDR3 shown as SEQ ID No. 13.

2. The method according to claim 1, wherein the blood sample is a serum or plasma sample.

3. A method for an identification of therapeutic efficacy of tumor treatment, comprising:

obtaining blood samples from a subject at a first time and a second time;

determining a concentration of GAPDH in each of the blood samples by a sandwich ELISA; and comparing the concentration of GAPDH in the blood samples at the first time and the second time, wherein when the concentration of GAPDH in the blood sample at the second time is lower than that at the first time, and a percentage of decrease reaches or exceeds a set reference value, then it is determined that the therapeutic treatment is effective;

wherein when the concentration of GAPDH in the blood sample at the second time is increased in comparison to that at the first time, is not significantly different from that at the first time or a percentage of increase does not reach or exceed the set reference value, then it is determined that the therapeutic treatment is not effective, wherein the first time and the second time are respectively a beginning and an end of a period; or the first time and the second time are respectively before and after receiving a treatment, wherein the set reference value is 30%, wherein an amino acid sequence of GAPDH is shown as SEQ ID No. 1, the sandwich ELISA is performed by a capture antibody and a detection antibody, the capture antibody binds to N-terminal amino acids 40-160 of the GAPDH amino acid sequence for capturing GAPDH from each of the blood samples, and the detection antibody binds to N-terminal amino acids 180-335 of the GAPDH amino acid sequence for measuring the concentration of GAPDH, wherein the capture antibody comprises heavy chain variable region and light chain variable region, the heavy chain variable region comprises CDR1 shown as SEQ ID No. 2, CDR2 shown as SEQ ID No. 3 and CDR3 shown as SEQ ID No. 4, the light chain variable region comprises CDR1 shown as SEQ ID No. 5, CDR2 shown as SEQ ID No. 6 and CDR3 shown as SEQ ID No. 7, the detection antibody comprises heavy chain variable region and light chain variable region, the heavy chain variable region comprises CDR1 shown as SEQ ID No. 8, CDR2 shown as SEQ ID No. 9 and CDR3 shown as SEQ ID No. 10, the light chain variable region comprises CDR1 shown as SEQ ID No. 11, CDR2 shown as SEQ ID No. 12 and CDR3 shown as SEQ ID No. 13.

4. The method according to claim 3, wherein the blood sample is a serum or plasma sample.

5. The method according to claim 3, wherein the tumor comprises a liver cancer, a lung cancer, a breast cancer, a gastric cancer, an esophageal cancer, a colorectal cancer, a pancreatic cancer, a cervical cancer, a lymphoma, or a thyroid tumor.

6. The method according to claim 3, wherein the identification of therapeutic efficacy of tumor comprises a detection of GAPDH and at least one additional tumor marker in the blood sample, and the at least one additional tumor marker comprises AFP, CEA, CA125, CA15-3, CA19-9, CA72-4, CA242, CYFRA21-1, AFU, POA, and TSGF.

7. An assay kit for tumor screening, evaluating risk of tumor development and identification of therapeutic efficacy of tumor treatment in subjects, comprising:

a reagent used to detect GAPDH in a blood sample, wherein an amino acid sequence of GAPDH is shown as SEQ ID No. 1;

wherein the reagent comprises a capture antibody and a detection antibody, the capture antibody binds to N-terminal amino acids 40-160 of the GAPDH amino acid sequence for capturing GAPDH from the blood sample, and the detection antibody binds to N-terminal amino acids 180-335 of the GAPDH amino acid sequence for measuring the concentration of GAPDH, wherein the capture antibody comprises heavy chain variable region and light chain variable region, the heavy chain variable region comprises CDR1 shown as SEQ ID No. 2, CDR2 shown as SEQ ID No. 3 and CDR3 shown as SEQ ID No. 4, the light chain variable region comprises CDR1 shown as SEQ ID No. 5, CDR2 shown as SEQ ID No. 6 and CDR3 shown as SEQ ID No. 7, and wherein the detection antibody comprises heavy chain variable region and light chain variable region, the heavy chain variable region comprises CDR1 shown as SEQ ID No. 8, CDR2 shown as SEQ ID No. 9 and CDR3 shown as SEQ ID No. 10, the light chain variable region comprises CDR1 shown as SEQ ID No. 11, CDR2 shown as SEQ ID No. 12 and CDR3 shown as SEQ ID No. 13.

8. The kit according to claim 7, wherein the kit is performed by an enzyme-linked immunosorbent assay.

9. The kit according to claim 8, wherein the reagent used to detect GAPDH in the blood sample includes a pair of antibodies specifically binding to GAPDH or a polypeptide fragment thereof.

10. The kit according to claim 9, wherein the polypeptide fragment of GAPDH comprises a polypeptide fragment consisting of N-terminal amino acids 40-160 of the GAPDH amino acid sequence, or a polypeptide fragment consisting of N-terminal amino acids 180-335 of the GAPDH amino acid sequence.

11. The kit according to claim 7, the kit further comprises: a 96-well ELISA Plate, a standard dilution solution, a sample dilution solution, a concentrated solution for washing, a color-developing solution and a stopping solution.

* * * * *

SEQUENCE LISTING

```
<160> NUMBER OF SEQ ID NOS: 13

<210> SEQ ID NO 1
<211> LENGTH: 335
<212> TYPE: PRT
<213> ORGANISM: Homo sapiens

<400> SEQUENCE: 1

Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205
```

```
Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
                245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 2
<211> LENGTH: 8
<212> TYPE: PRT
<213> ORGANISM: Artificial Sequence
<220> FEATURE:
<223> OTHER INFORMATION: CDR1 of Heavy Chain Variable Region of Capture
      Antibody

<400> SEQUENCE: 2

Gly Phe Ser Leu Thr Asn Tyr His
1               5

<210> SEQ ID NO 3
<211> LENGTH: 7
<212> TYPE: PRT
<213> ORGANISM: Artificial Sequence
<220> FEATURE:
<223> OTHER INFORMATION: CDR2 of Heavy Chain Variable Region of Capture
      Antibody

<400> SEQUENCE: 3

Ile Gly Ile Ser Gly Thr Pro
1               5

<210> SEQ ID NO 4
<211> LENGTH: 10
<212> TYPE: PRT
<213> ORGANISM: Artificial Sequence
<220> FEATURE:
<223> OTHER INFORMATION: CDR3 of Heavy Chain Variable Region of Capture
      Antibody

<400> SEQUENCE: 4

Ala Arg Leu Thr Gly Asp Gly Gly Asp Leu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: CDR1 of Light Chain Variable Region of Capture
      Antibody

<400> SEQUENCE: 5

Glu Asp Ile Glu Asn Tyr
```

```
<210> SEQ ID NO 6
<211> LENGTH: 2
<212> TYPE: PRT
<213> ORGANISM: Artificial Sequence
<220> FEATURE:
<223> OTHER INFORMATION: CDR2 of Light Chain Variable Region of Capture
      Antibody

<400> SEQUENCE: 6

Trp Thr
1

<210> SEQ ID NO 7
<211> LENGTH: 14
<212> TYPE: PRT
<213> ORGANISM: Artificial Sequence
<220> FEATURE:
<223> OTHER INFORMATION: CDR3 of Light Chain Variable Region of Capture
      Antibody

<400> SEQUENCE: 7

Gln Ser Ala His Tyr Ser Ser Ser Ser Tyr Gly Trp Ala
1               5                   10

<210> SEQ ID NO 8
<211> LENGTH: 8
<212> TYPE: PRT
<213> ORGANISM: Artificial Sequence
<220> FEATURE:
<223> OTHER INFORMATION: CDR1 of Heavy Chain Variable Region of
      Detection Antibody

<400> SEQUENCE: 8

Gly Phe Ser Leu Ser Ser Tyr Tyr
1               5

<210> SEQ ID NO 9
<211> LENGTH: 8
<212> TYPE: PRT
<213> ORGANISM: Artificial Sequence
<220> FEATURE:
<223> OTHER INFORMATION: CDR2 of Heavy Chain Variable Region of
      Detection Antibody

<400> SEQUENCE: 9

Met Asn Val Val Thr Gly Ser Ala
1               5

<210> SEQ ID NO 10
<211> LENGTH: 15
<212> TYPE: PRT
<213> ORGANISM: Artificial Sequence
<220> FEATURE:
<223> OTHER INFORMATION: CDR3 of Heavy Chain Variable Region of
      Detection Antibody

<400> SEQUENCE: 10

Ala Arg Val Asp Ala Ser Gly Ser Gly Tyr Phe Arg Leu Asp Leu
1               5                   10                  15

<210> SEQ ID NO 11
<211> LENGTH: 6
<212> TYPE: PRT
<213> ORGANISM: Artificial Sequence
<220> FEATURE:
<223> OTHER INFORMATION: CDR1 of Light Chain Variable Region of
```

```
                        -continued

Detection Antibody

<400> SEQUENCE: 11

Gln Ser Ile Gly Ser Trp
1               5

<210> SEQ ID NO 12
<211> LENGTH: 2
<212> TYPE: PRT
<213> ORGANISM: Artificial Sequence
<220> FEATURE:
<223> OTHER INFORMATION: CDR2 of Light Chain Variable Region of
      Detection Antibody

<400> SEQUENCE: 12

Arg Ala
1

<210> SEQ ID NO 13
<211> LENGTH: 13
<212> TYPE: PRT
<213> ORGANISM: Artificial Sequence
<220> FEATURE:
<223> OTHER INFORMATION: CDR3 of Light Chain Variable Region of
      Detection Antibody

<400> SEQUENCE: 13

Gln Gln Thr Phe Asp Tyr Gly Asp Leu Gly Ser Asn Ala
1               5                   10
```